United States Patent [19]
Sachse

[11] Patent Number: 6,053,897
[45] Date of Patent: Apr. 25, 2000

[54] APPARATUS FOR MAINTAINING THE PATENCY OF URINE FLOW THROUGH THE URETHRA

[76] Inventor: Hans E. Sachse, 90425, Nuremberg, Germany

[21] Appl. No.: 08/743,078

[22] Filed: Nov. 4, 1996

[30] Foreign Application Priority Data

Nov. 3, 1995 [DE] Germany .......................... 195 40 919

[51] Int. Cl.[7] .................................................. A61M 5/00
[52] U.S. Cl. ........................ 604/264; 604/280; 604/247; 604/93; 128/840
[58] Field of Search ............................. 604/280, 54, 264, 604/265, 247, 93, 246; 128/840, 844

[56] References Cited

U.S. PATENT DOCUMENTS 5,209,726  5/1993  Goosen ..................................... 604/54

*Primary Examiner*—Wynn Wood Coggins
*Assistant Examiner*—N. Kent Gring
*Attorney, Agent, or Firm*—Keil & Weinkauf

[57] ABSTRACT

An apparatus for maintaining the patency of urine flow through the human urethra, having an intra-urethral catheter (IUC), which has a potential through flow for the urine that extends over its length. The length of the IUC is shorter than the length of the urethra, and the IUC does not protrude from the urethral orifice at either of its ends. A transport means for the insertion of the IUC into the urethra is also associated with the apparatus. Devices are further provided on the ends of the IUC for producing a detachable connection between the IUC and the transport means. The IUC is disposed in the region of the urethra which passes through the prostate gland and the inner sphincter.

20 Claims, 9 Drawing Sheets

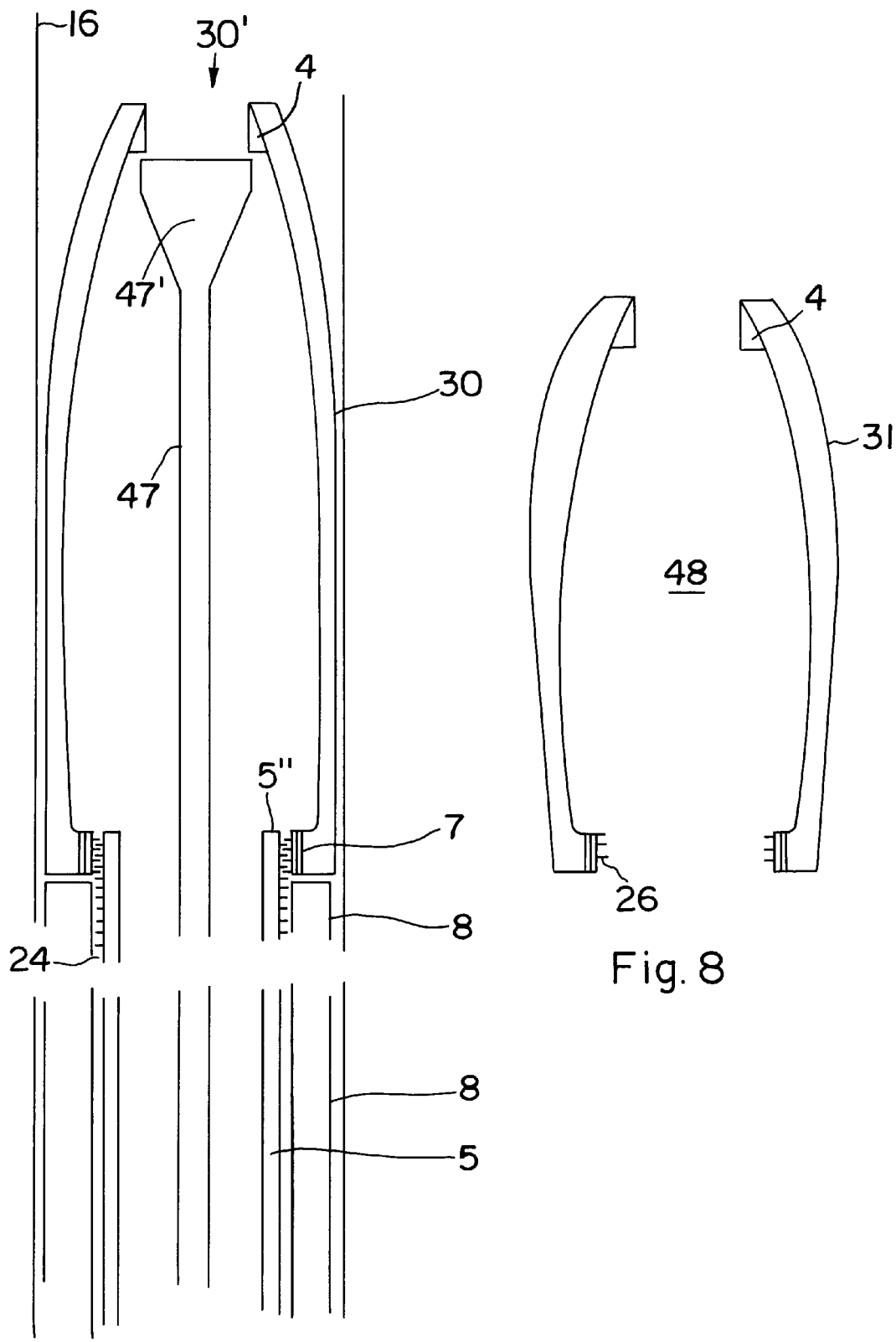

APPARATUS FOR MAINTAINING THE PATENCY OF URINE FLOW THROUGH THE URETHRA

BACKGROUND OF THE INVENTION

The invention relates to an apparatus for maintaining the patency of urine flow through the human urethra, having an intra-urethral catheter (IUC), which has a potential through flow for the urine that extends over its length, whose length is shorter than the length of the urethra, and which does not protrude from the urethral orifice by either of its ends; a transport means for the insertion of the IUC into the urethra is also associated with the apparatus. U.S. Pat. No. 4,973,401 and European Patent Application 0 593 948 disclose apparatuses of this kind. The intra-urethral catheter (for the sake of simplicity, always referred to below as the IUC) is disposed in the region of the urethra which passes through the prostate gland and the inner sphincter. Inserting metal spirals through the urethra into the desired position of the urethra region is also known. The insertion and removal of the aforementioned metal spirals and of the IUC is very costly. As a rule, endoscopic measures are required, along with the use of hooks or forceps, and an anesthetic. By and large, this is very costly and time-consuming, and is also correspondingly stressful for the patient.

The goal which is thereby achieved, of keeping the urethra open while at the same time preventing ascendant infections of the urinary tract, therefore involves corresponding disadvantages. The aforementioned ascendant infections resulted when a dwelling catheter was used, which was inserted through the urethra to the point that its tip reached the bladder so that the bladder urine could be drawn outward by means of the permanent catheter protruding from the urethral orifice. When drawing off of urine with a catheter in this way, after a short time, the serious disadvantage already became apparent that infectious germs ascended from the urethral orifice toward the bladder along the catheter walls and infected the prostate gland and bladder. Healing infections of this kind is difficult, lengthy, and costly and antibiotics resistant pathogens can be impossible to cure.

OBJECT AND SUMMARY OF THE INVENTION

The stated object of the invention comprises embodying an apparatus which is simpler in comparison to the described, previously known apparatuses, cheaper to manufacture, and above all, more practicable to manipulate. Patient complaints are essentially reduced, in comparison to the implementation of apparatuses according to the prior art, and in addition, the embodiments and potential uses of the IUC are improved.

In order to attain this stated object it is first provided that on at least one end of the IUC, which is its end oriented toward the doctor (distal end) when inserted in the body, and on the end of the transport means oriented toward the patient (proximal end), devices are provided which correspond to each other and are for producing a detachable connection between IUC and transport means, and that an actuator is provided for producing and detaching the connection and leads outward so that it can be grasped and manipulated by the doctor. With this, the insertion and removal of the IUC into or out of the desired position is essentially easier to execute than with the prior art explained, for example according to U.S. Pat. No. 4,973,301. In particular, the equipment expenditure required for this is lower and can be kept small in diameter so that the relevant transport means can be inserted and removed without the danger of an overexpansion with injury to the urethra and without the corresponding pain for the patient. The insertion of an endoscope or endoscope shaft is not necessary. In most cases, a control by feel or an X-ray control is sufficient to find out at in which position in the urethra the IUC is disposed. If the desired positioning is achieved, then the treating physician merely needs to detach the connection between IUC and transport means using the aforementioned actuator and then remove the transport means from the urethra. For the case in which the IUC is inadvertently inserted too far into the urethra, by means of the transport means, it can be pulled back again for a corresponding distance in the direction of the urethral orifice until it assumes the desired position. With the teaching of U.S. Pat. No. 4,973,301 and European Patent Application 0 593 948, this is not possible or is only possible with the risk of an uncertainty since there, only one string which is affixed to the distal end of the IUC is used for the removal of the IUC in the direction of the urethral orifice, which can only be grasped if the transport means has been previously removed from the urethra. Furthermore, a string of this kind represents a constant infection transmitter for an ascendant infection. While the aforementioned references for the insertion of the IUC into the urethra provide for a relatively costly construction and furthermore must have yet another means, namely the aforementioned string, for the removal of the IUC in the direction of the urethral orifice, with the subject of the invention, the transport of the IUC, both toward the bladder and toward the urethral orifice, is carried out with one and the same transport means. The IUC does not protrude outward from the urethra. This is true for all embodiments according to the invention. In this connection, it is also essentially more comfortable for the patient to have an IUC in his body which IUC is only relatively short rather than a long permanent catheter, which extends from the bladder and outward through the entire urethra. The through flow through the IUC can be a central opening. It is also possible to have a plurality of through flow conduits extending in the longitudinal direction of the IUC.

In a preferred embodiment, the IUC according to the invention is matched in its effective length to the length of the constriction of the urethra to be removed or to the length of a particular section of the urethral region, and the outer diameter of the IUC approximately corresponds to the inner diameter of a healthy urethra with no constriction. An insertion piece of this kind is shorter than the urethra and holds on by itself in the urethra. It has one or a plurality of through flow openings and is preferably tubular. As can be seen from embodiments below, this insertion piece can be matched to particular use purposes and is inserted with the respective transport means by the doctor through the urethra into its narrowed place, e.g. in an operated urethral constriction or into the respectively desired position. After this insertion, the connection is detached between the IUC and the transport means (in actual use, also described in some areas as a urethral stent).

In another preferred embodiment, the apparatus is used to prevent ascendant infections in the region of the prostate gland. For the sake of brevity, this intra-urethral catheter is called an "IUCI". When the IUCI is inserted, this provides a deliberate incontinence over the length of the urethral region in the prostate gland and both of the sphincters. Maintaining patency of both sphincters and the prostate gland provides for an incontinence and hence a constant potential discharge of urine from the bladder outward through the urethra in a particularly safe and advantageous manner. In this way, an ascendant infection of the urinary tract is simultaneously prevented, which also exists in all the rest of the possible embodiments of the invention since in these cases, too, the urine discharging from the relevant IUC travels along the inner wall of the urethra and washes germs out again, ascending from the urethral orifice. Patients who are in an intensive care unit and run an increased risk of infection often require an uninterrupted discharge of bladder urine and the strict prevention of an ascendant infection of the urinary tract.

Instead of the aforementioned apparatus of the preceding paragraph, an effective length of the IUC can also be provided in such a way that in the inserted position, it extends only over the length of the prostate gland including the inner sphincter, provided that this is medically indicated. The outer sphincter is not held open here, i.e. it remains closed in the micturition pause. The aforementioned apparatus of the invention is abbreviated as "IUCP". With it, in a deliberate fashion, only the aforementioned region is held open. An IUCP of this kind can be used when an enlarged prostate gland presents obstructions to bladder emptying and causes an attendant constriction of the urethra. The patient can start or stop the flow of urine with his outer sphincter, which is intact.

In an embodiment called an "IUCU", it is also possible to dispose the IUC in the region of the frontal urethra, that is the region excluding that of the prostate gland. An IUC is used for deliberately maintaining the patency of a section of the frontal urethra after a surgery in which a constriction of the urethra has been removed. In a surgically removed constriction of the urethra, the apparatus of the invention in the form of the IUCU should prevent the urethra in this region from becoming blocked again until the surrounding tissue has permanently regained its strength. In this instance, the IUCU merely extends over the length of the relevant constriction or the length of the region of the urethra operated upon.

It is up to the judgement of the doctor which of the aforementioned embodiments of the IUC he will respectively employ. In all cases, it is advantageously possible to move the IUC into and out of its working position.

All aforementioned embodiments of the IUC can be inserted into the urethra to the desired position with the transport means. The outer diameter of the transport means according to the invention is under no circumstances greater than the diameter of the IUC. Therefore, the urethra is essentially expanded less with the invention than with the use of means according to the prior art.

In another preferred embodiment of the invention an IUCU has a plunger (47) for changing the length of the tube (30, 31), which plunger engages the end of the tube (30) oriented toward the patient, while the end of the tube (30) oriented toward the doctor is detachably connected to the transport means. This embodiment is particularly well suited in terms of its positioning inside a constriction of the urethra, which has been operated upon, because of the alteration of the configuration of the IUCU made possible as a result.

A transport catheter may be provided as a preferred embodiment of the transport means for inserting the IUC and removing it once again. In contrast to the standard permanent urethral catheter mentioned at the beginning, which is used for the discharge of urine, the transport catheter provided here is disposed inside the urethra for only a short period, namely when inserting the IUC into the urethra and removing it once again. The transport catheter carries both its portion of the detachable connection means and the actuation device to be manipulated from the outside, with which the connection to the end of the IUC oriented toward the doctor can be produced and detached.

The invention moreover relates to various embodiments of the aforementioned connecting means of the IUC with the transport catheter or devices carried by it, which are for producing or detaching the aforementioned connection. Thus a guide can be provided for example inside the transport catheter, which guide is detachably screwed on the one hand to the transport catheter and on the other hand to the end of the IUC oriented toward the doctor.

Other embodiments and features of the invention are referred to in the remaining dependent claims as well as in the description below and the accompanying drawings of potential embodiments according to the invention. Each of the drawings is a longitudinal section.

BRIEF DESCRIPTION OF THE DRAWINGS

FIGS. 3–10, which are explained below, are each shown in a larger scale in comparison to FIGS. 1 and 2;

FIG. 3 shows an exemplary embodiment (IUCI) of the invention, with a screw connection;

FIG. 4 shows a modification of the embodiment according to FIG. 3, with a directional probe;

FIG. 5 shows another exemplary embodiment of the invention, with a clamp connection;

FIG. 6 shows another embodiment of the invention, with a balloon connection;

FIGS. 7 and 8 show another embodiment of the invention with an IUCU, which can be changed in length and cross sectional diameter, for the constriction of the urethra operated upon; and FIGS. 9 and 10 each show other embodiments of the invention.

DESCRIPTION OF THE PREFERRED EMBODIMENTS

Figure 1:
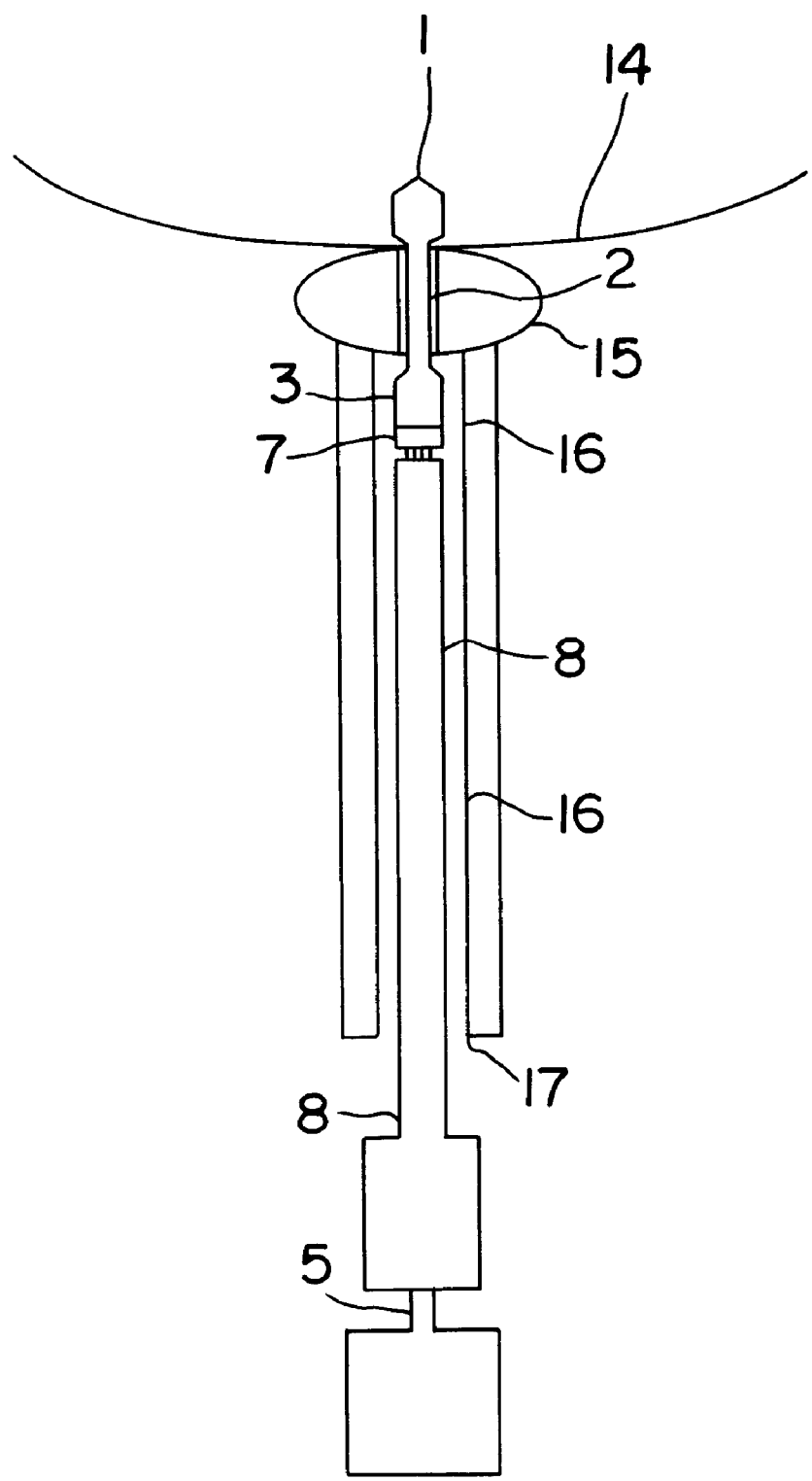
FIG. 1 shows the principle of the invention including the region of the bladder adjacent to the prostate gland, having an inserted transported catheter, with the transport catheter and IUC seen from the top.

The temporary holding open of the urine discharge from the bladder by means of an IUCI is represented, and in fact in a simple way (be it with or without optical control), in a first exemplary embodiment by means of the positioning of an IUCI of this kind in the region of the prostate gland with the inner and outer sphincter of the urethra. An IUCI, which in this case is relatively rigid, comprises a preferably thickened end 1 oriented toward the patient, an end 3, which is likewise preferably thickened and is oriented toward the doctor, and a section 2 disposed between them, which is preferably narrowed. One end or both ends of the IUC are embodied as mating connection means for connecting the IUC to the transport means. Several potential embodiments of this kind of connection means are explained below. The parts 1–3 of this approximate "dumbbell-shape" are made of a plastic which corresponds to the desired hardness. In contrast to the aforementioned prior art, the thickened ends of this one are compact. They can, however, be embodied like one of the known possible retention devices for catheter tips, such as the one according to Malékot, Pezzer, and Casparete. The IUC, in this case an IUCI, has through flows or conduits passing through in its longitudinal direction, here a central conduit 22, through which the bladder urine 25 flows out of the bladder 14 into the lumen 29 of the urethra 16 and comes out from there, e.g. into a condom urinal 18 surrounding the urethral orifice 17. Clearly, the IUCI 1–3 passes through the region 15 of the prostate gland with the inner sphincter, which is not separately shown in the drawing and is disposed approximately in the position 15'. This is also true for the region of the outer sphincter 15". Consequently, the entire bladder sphincter region is held open by the IUCI in order to ensure the aforementioned discharge of urine. If necessary, according to the length of the IUC in the form of an IUCP, just the prostatic urethra and the region of the inner sphincter can be held open (not shown).

Figure 2:
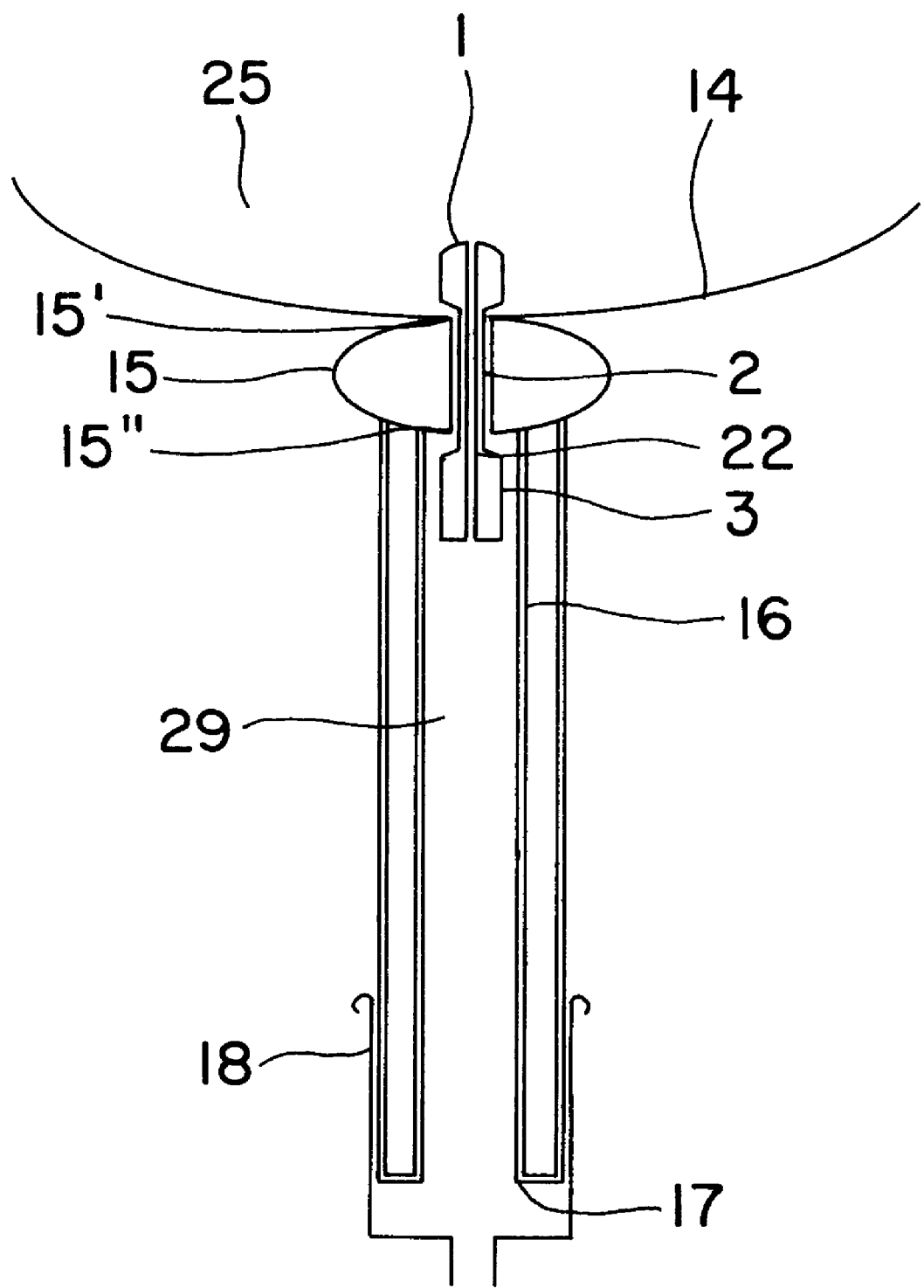
FIG. 2 shows the depiction according to FIG. 1, with an additional condom urinal after the removal of the transport catheter, with diverted urine.

The IUCI is brought into its position shown in FIGS. 1 and 2 by means of a transport catheter 8. Between the transport catheter 8, or a device carried along by it, on the one hand and the end of the IUC oriented toward the doctor on the other hand, a detachable connection is provided, which is only schematically indicated in FIG. 1 with the number 7 and which is locked for the insertion of the IUC into the desired position (see also the variants of the invention according to FIGS. 7 and 8) and is then detached in order to be able to remove the transport catheter 8 and the device, which if necessary is provided on it, from the urethra.

The IUC can also have an embodiment and shape other than that shown in FIGS. 1 and 2. In general, a transport means according to the invention can be inserted together with every IUC which fulfills the requirements of claim 1, and has a connecting means on at least one end, which can be detachably coupled to the affiliated mating connection means of the transport means. Therefore not only can the IUCs explained in the exemplary embodiments be used; the invention can be used with all possible IUCs, e.g. even with IUCs which are already on the market, as long as they are equipped with a potential connection to the affiliated transport means.

Furthermore, another embodiment of the IUC can also be provided for the case in which it is not disposed inside the urethral region of the prostate gland and its sphincter, but is disposed in the frontal region of the urethra, called an IUCU here (see FIGS. 7, 8, and the affiliated explanation).

According to FIG. 2a, with its end oriented toward the doctor, the IUC can protrude farther into the urethra, i.e. toward the urethral orifice, than is shown in FIG. 2. This embodiment can be selected if an elongation of the relevant IUC end is required or at least advantageous for the detachable coupling of the transport means.

Figure 3:
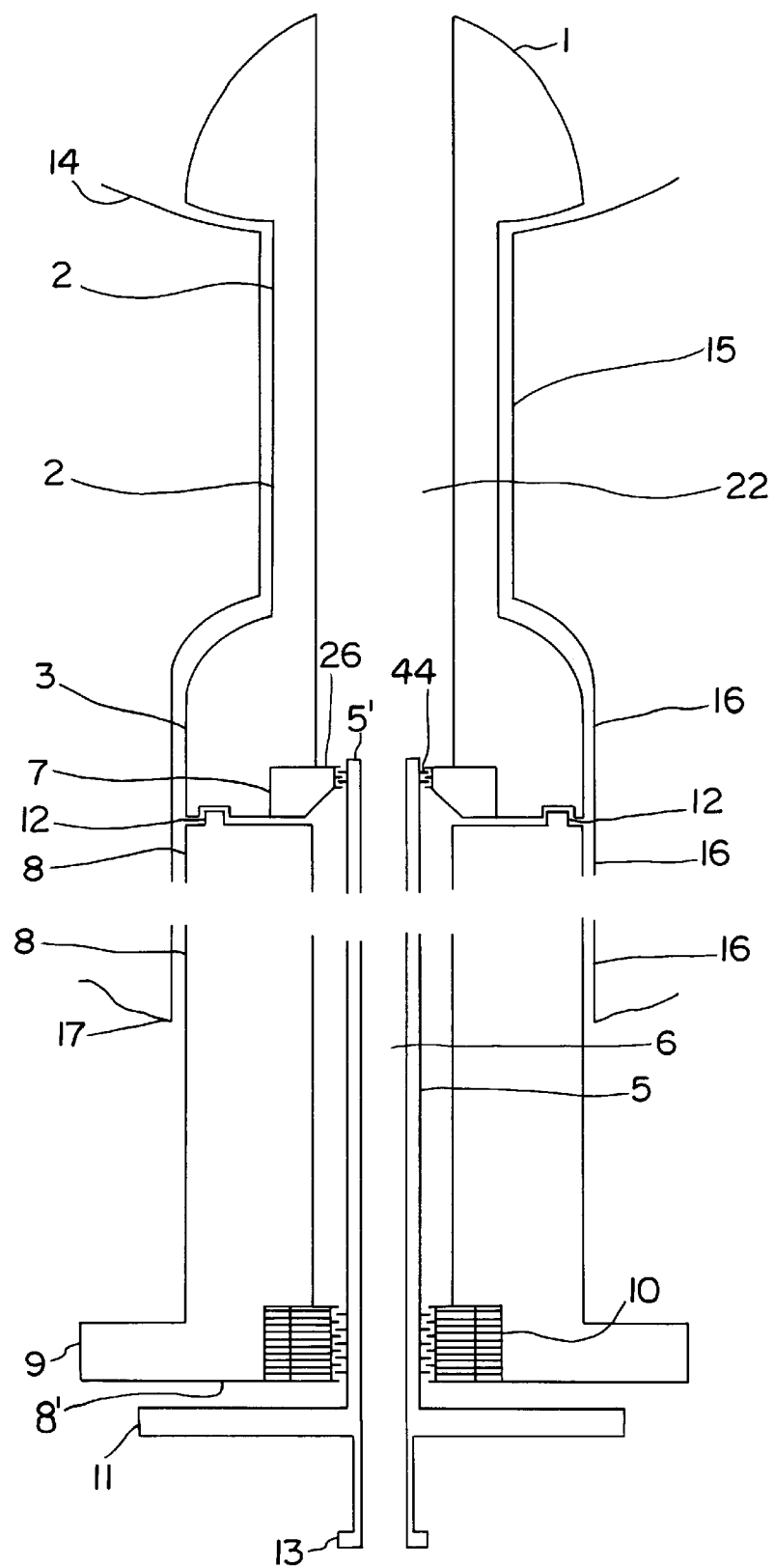

FIG. 3 shows the principle of the embodiment of an IUCI according to FIGS. 1 and 2, with a detachable connection in the form of a screw connection between the IUCI 1–3 on the one hand and the transport catheter 8 on the other. For this, in the region 10 oriented toward the doctor, a guide 5 is screwed to the transport catheter 8. In addition, there is a screw connection between the IUCI and the end 5' of the guide oriented toward the patient, in fact in this case by means of a metal ring 26 which is firmly embedded in the end 3 of the IUCI oriented toward the doctor and has an internal thread, which engages the external thread 44 of the guide end 5'. If the aforementioned screw connections 10 and 7 are achieved, then the IUCI can be brought into the desired position according to FIG. 3, i.e. into the urethra, by inserting the transport catheter 5 into the urethra with the aid of its handle 9 and 11. Then the screw connections 10 and 7 are detached by rotating the handle 11 of the guide 5. The guide 5 and also the transport catheter 8 can be removed from the urethra.

The guide 5 can be embodied as a hollow guide with a lumen 6 and on the end oriented toward the doctor, and therefore outside the patient, can have an attachment fitting 13 for the injection of a lubricant or a radiographic contrast medium.

Between the end 3 of the IUC oriented toward the doctor and the end of the transport catheter 8 oriented toward the patient, a locking device 12 can be provided which comprises projections on the transport catheter and recesses on the IUC for receiving these projections and which prevents an unintentional rotation of the IUC and the transport catheter in relation to each other around their common longitudinal axis.

Figure 4:
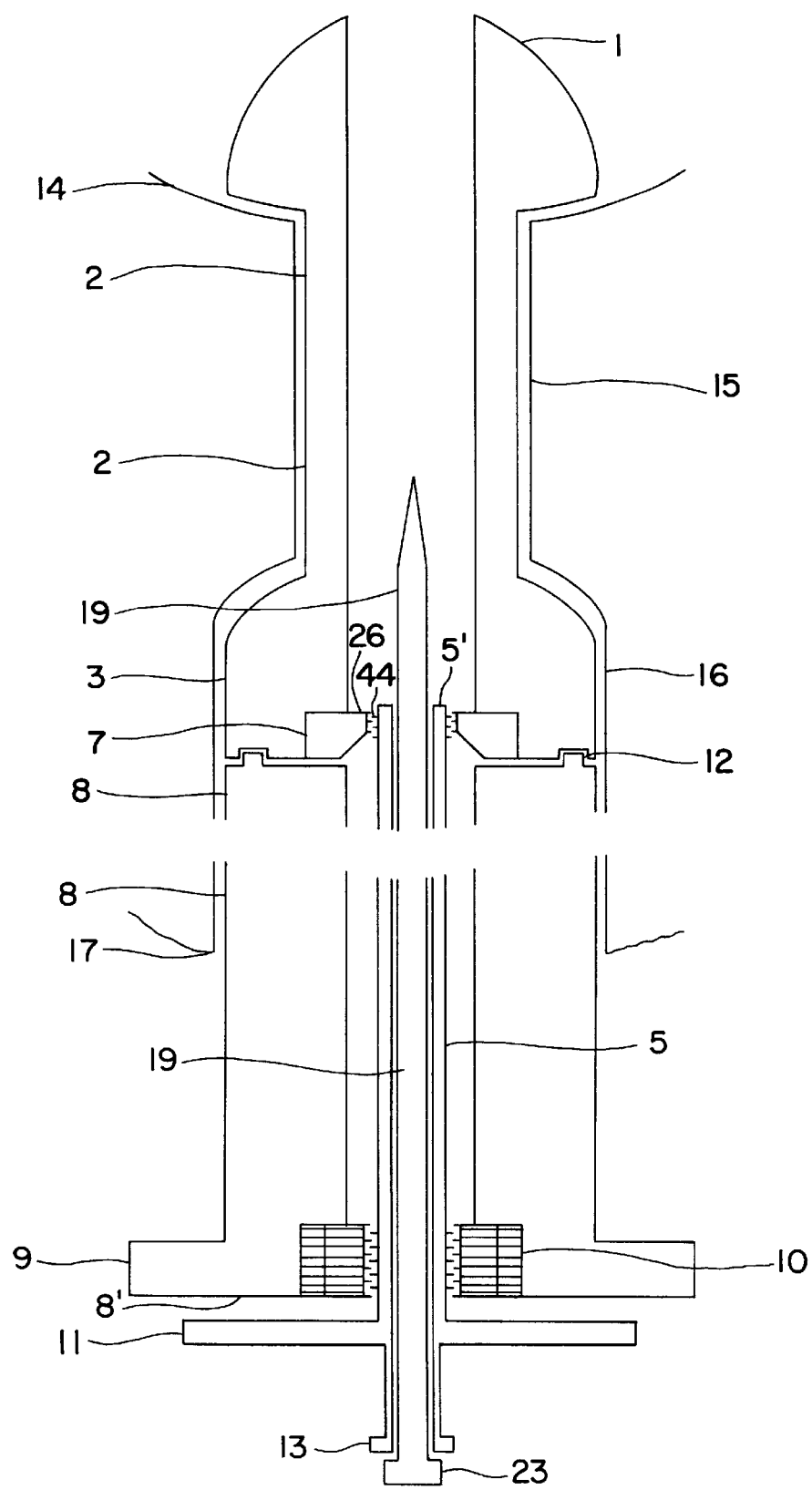

The embodiment according to FIG. 4 essentially corresponds to the embodiment according to FIG. 3. In addition, another directional probe 19 is provided in the lumen 6 of the hollow guide 5, which probe ends in a handle 23 on the end oriented toward the doctor and in a tip on the end oriented toward the patient. This directional probe facilitates the centering of the guide for the removal of the IUC with its end 5' when being inserted into the threaded part of the IUC, i.e. for the engagement of the two threads 26 and 44 with each other, and the funnel-shaped end 3 of the IUC, which end, in this exemplary embodiment, is embodied by the underside of the metal ring 26 (see also FIG. 3), has a positive effect.

At this point it should be noted that in the embodiments according to FIGS. 3 and 4, the lower screw connection 10 between the guide 5 and the transport catheter could be left out provided that with its handle 11 or another stop, the guide rests directly against the lower end 8' of the transport catheter 8.

Figure 5:
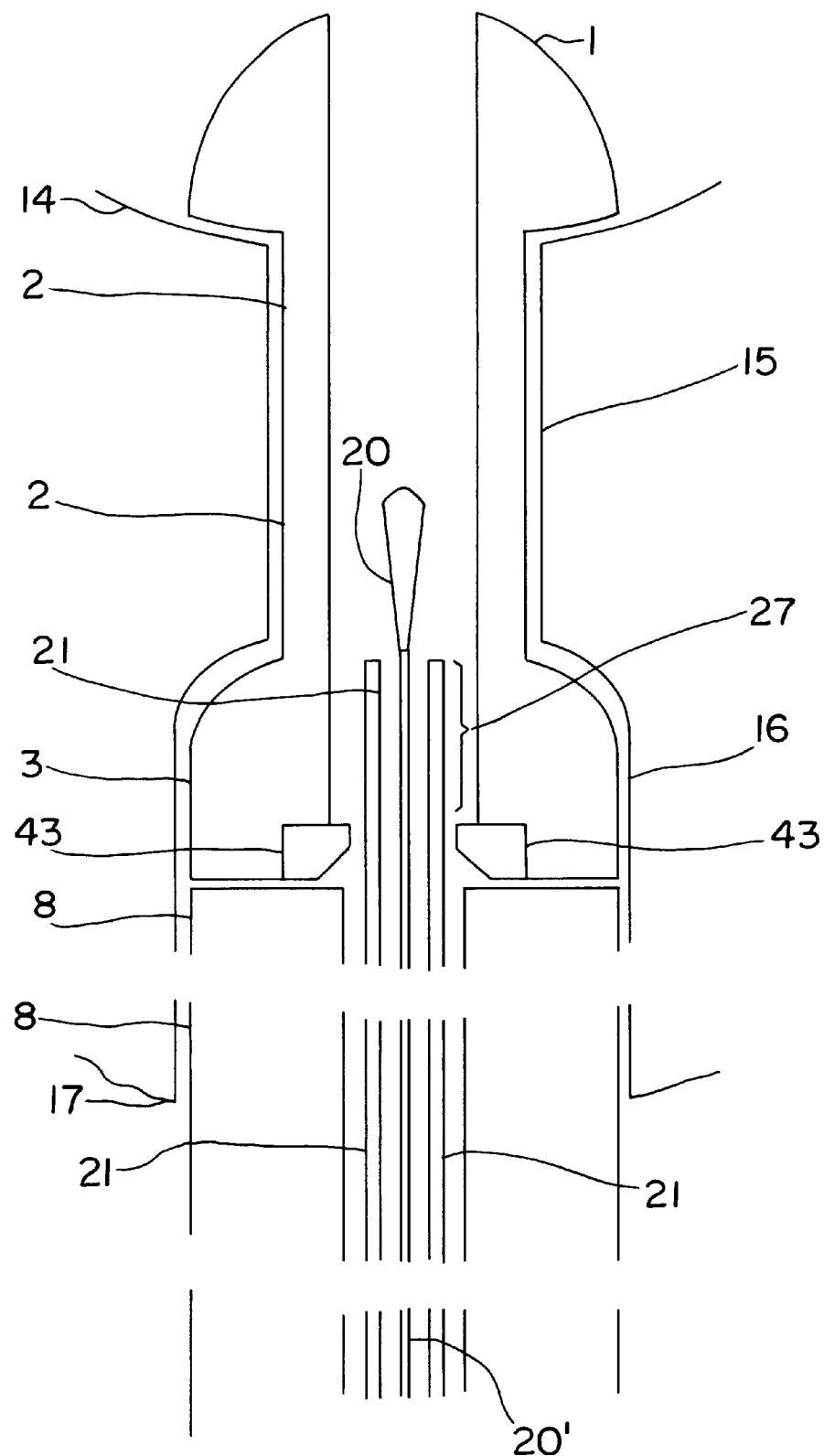

In the embodiment according to FIG. 5, a clamp device is used to achieve the detachable connection of the IUC with the transport catheter 8. In addition, instead of the guide 5, a retractor sleeve 21 and a retracting wedge 20 which can be moved in the longitudinal direction of the sleeve are provided inside the lumen of the transport catheter, and the wedge can be moved in its longitudinal direction via its shaft 20' by a handle which is disposed outside the urethra and is not shown in the drawing. The retractor sleeve 21 is firmly connected to the transport catheter 8. This can take place outside the urethra (not shown) by means of clamping the transport catheter to the retractor sleeve. Instead of this, the transport catheter can also be screwed to the retractor sleeve outside the urethra. The region 27 of the retractor sleeve 21 disposed toward the bladder in FIG. 5 is embodied so that it spreads out, for example by means of longitudinal slots, and rests against the stop 43 or also merely against the inner wall of the IUC in a clamping manner when the retractor wedge 20 is pulled downward. In this clamped position, the retractor wedge 20 is disposed approximately at the level of the stop 43. If the aforementioned connection is to be detached, then it is sufficient to move the shaft 20', and thus the retractor wedge 20, toward the bladder and into the position shown in FIG. 5. Parts 21, 20', and 20 are removed in opposition to the resistance of 8 and in this way, the connection is detached. The IUC is left behind.

Figure 6:
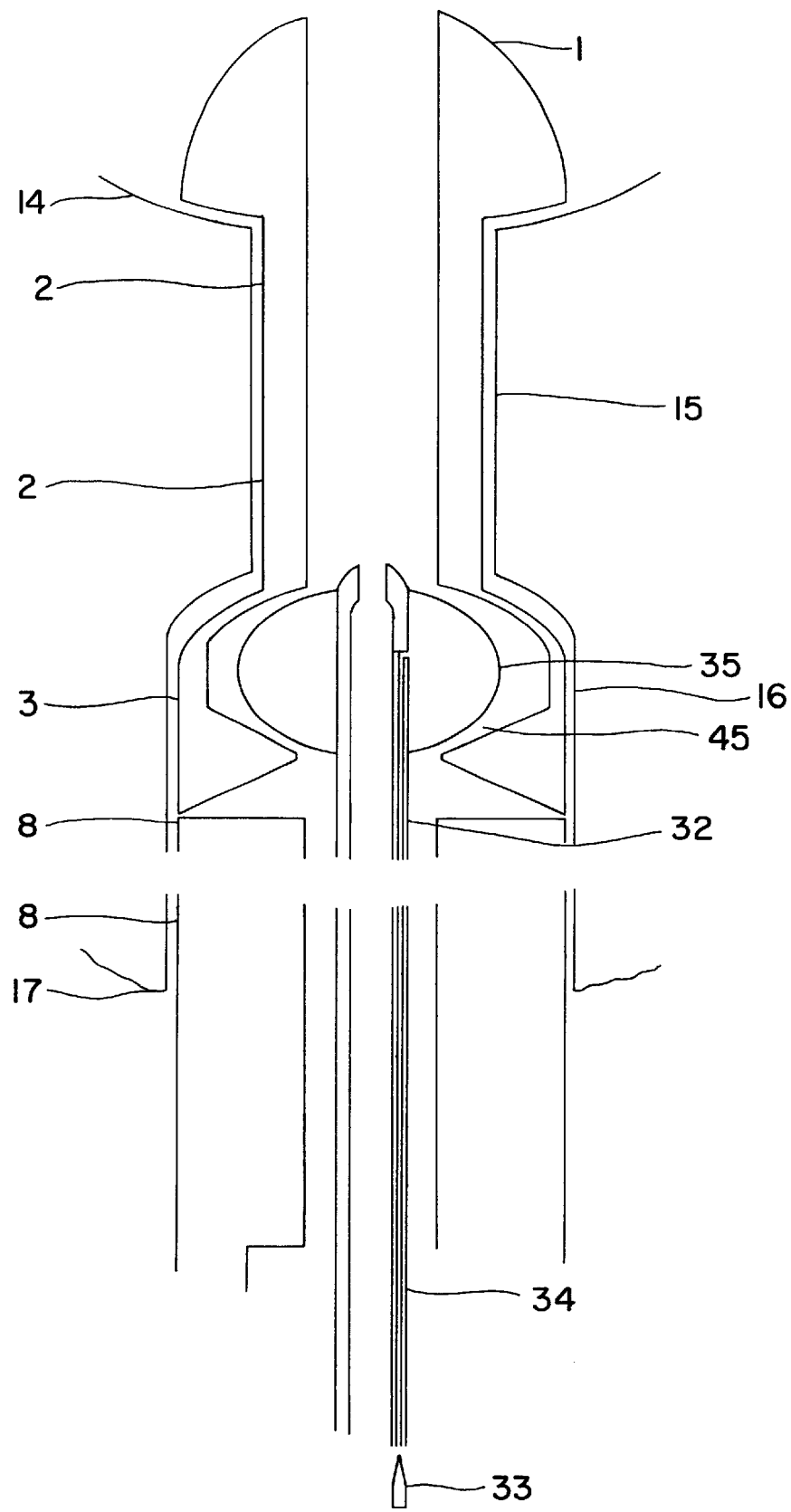

In the embodiment according to FIG. 6, instead of the guide 5, an inflatable balloon 35 of a balloon catheter 32 is used for the detachable connection of the transport catheter 8 to the IUCI 1–3. A filling conduit 34 can fill this balloon 35 with either gaseous or liquid medium; the end of the filling conduit 34 oriented toward the doctor can be closed by a stopper 33. The connection between urethral stent and transport catheter is produced when the balloon 35 is filled. The connection between the transport catheter 8 and the balloon catheter 32 is produced by clamping outside the urethra. If the gaseous or liquid medium is removed from the balloon by pulling out the stopper 33, then the balloon 35 collapses and the balloon catheter 32 can be taken out of the transport catheter 8. A directional probe, not shown, which is for the retrieval procedure, corresponds to the directional probe 19, and is for the balloon catheter 34, is moved through the catheter's lumen so that the directional probe tip protrudes from the balloon catheter tip and then, when moved toward the bladder, finds its way into the funnel-shaped end of the IUC of FIG. 6.

The exemplary embodiment in FIGS. 7 and 8 shows on the one hand, a different embodiment of the IUC and on the other hand, a different positioning of the IUC from the preceding exemplary embodiments. The IUCU here is not disposed in the urethral region which is surrounded by the prostate gland and its sphincter, but in the region of the frontal urethra. This is primarily necessary if the urethra is to be held open temporarily after an operation on a constriction of the urethra.

The IUCU, which is identified here by reference numeral 30 or 31 and is embodied as tubular, comprises an elastic material. On its end oriented toward the bladder, it is provided with a stop 4 and on its end oriented toward the doctor, is likewise provided with a stop which corresponds to the screw connection region 7 from the previous exemplary embodiments and has a thread 26 on the inside. A screw thread 44 is provided on a guide 5, which can be moved in its longitudinal direction in relation to the transport catheter, which thread can engage the thread 26.

A sliding bolt 47 is disposed inside the guide 5. After the guide 5 is screwed to the IUCU in the region 5", the IUC is correspondingly stretched as a result of the forward movement of the sliding bolt in the direction of the patient and the head 47' of the sliding bolt engaging a stop 4 of the IUC (see FIG. 7). This compensates for its more oval form, which is predetermined according to FIG. 8, and the IUCU in the shape according to FIG. 7 can be inserted into the region of the urethra operated upon. For the insertion procedure, guide 5 and sliding bolt 47 are connected firmly to each other outside the urethra (not shown). After correct positioning, the connection between guide 5 and sliding bolt is detached. With what is then insufficient stretching, the IUCU tries to return to its predetermined shape 31 (FIG. 8) and thus clamps itself in the operation region of the urethra. Another form of this extension can also be achieved by the fact that the guide 5 has a very long screw thread 24 and the tip 5" of this guide reaches into the tip region (not shown) of the IUCU when it is relaxed, and the guide 5 is screwed upward into the thread 24 until its tip 5" can stretch the IUCU via a stop or the like. On the other hand, if the guide 5 is screwed downward correspondingly far, then the IUCU 30 assumes the predetermined shape 31 once again. The guide 5 and the transport catheter are not shown in FIG. 8, but the inner wall 16 of the urethra is indicated in FIG. 7. The apparatus can also be made so that on its head, which is disposed at the top in FIG. 7, the sliding bolt 47 is embodied (not shown) so that the urine flows past this head in the direction of the arrow 30', into the inner chamber 48, and from there on to the urethral orifice.

The use of the IUC will be explained by means of FIG. 3, i.e. the embodiment in the form of an IUCI.

The assembly takes place before insertion of the IUCI. See FIG. 3. The shaft of the transport catheter 8 is mounted on the end of the IUCI oriented toward the doctor so that the pegs 12 protrude into the corresponding recesses of the IUCI. Then the screw thread of the guide 5 is screwed in simultaneously in the screw connection region 7 as well as 10. After this assembly, which can also be carried out by the manufacturer before sterilization, the IUCI is inserted, and the correct placement can be controlled by feel. Since the IUCI is "dumbbell-shaped" in this example and the sphincter region represents a functional constriction, when inserting, the experienced doctor will feel when the thinner middle region 2 of the IUCI slides into the sphincter/prostate gland region. The correct placement can furthermore be monitored optically or by X-ray control. Then the connection is detached between transport catheter and IUCI in one of the possible embodiments explained.

The removal of the IUCI is carried out by reinserting the transport catheter. Because of the routing of the urethra, when they are of the same outer diameter, the ends of the IUCI and the transport catheter already approach each other relatively accurately from the beginning. When the transport catheter is inserted, the directional probe 19, which can protrude more or less far from the transport catheter, makes it easier to more precisely adjust the two threads (as long as a screw connection is provided). With the coupling to one another of the IUCI and the transport catheter by means of a screw connection, the IUCI can be removed once again from the urethra.

Figure 9:
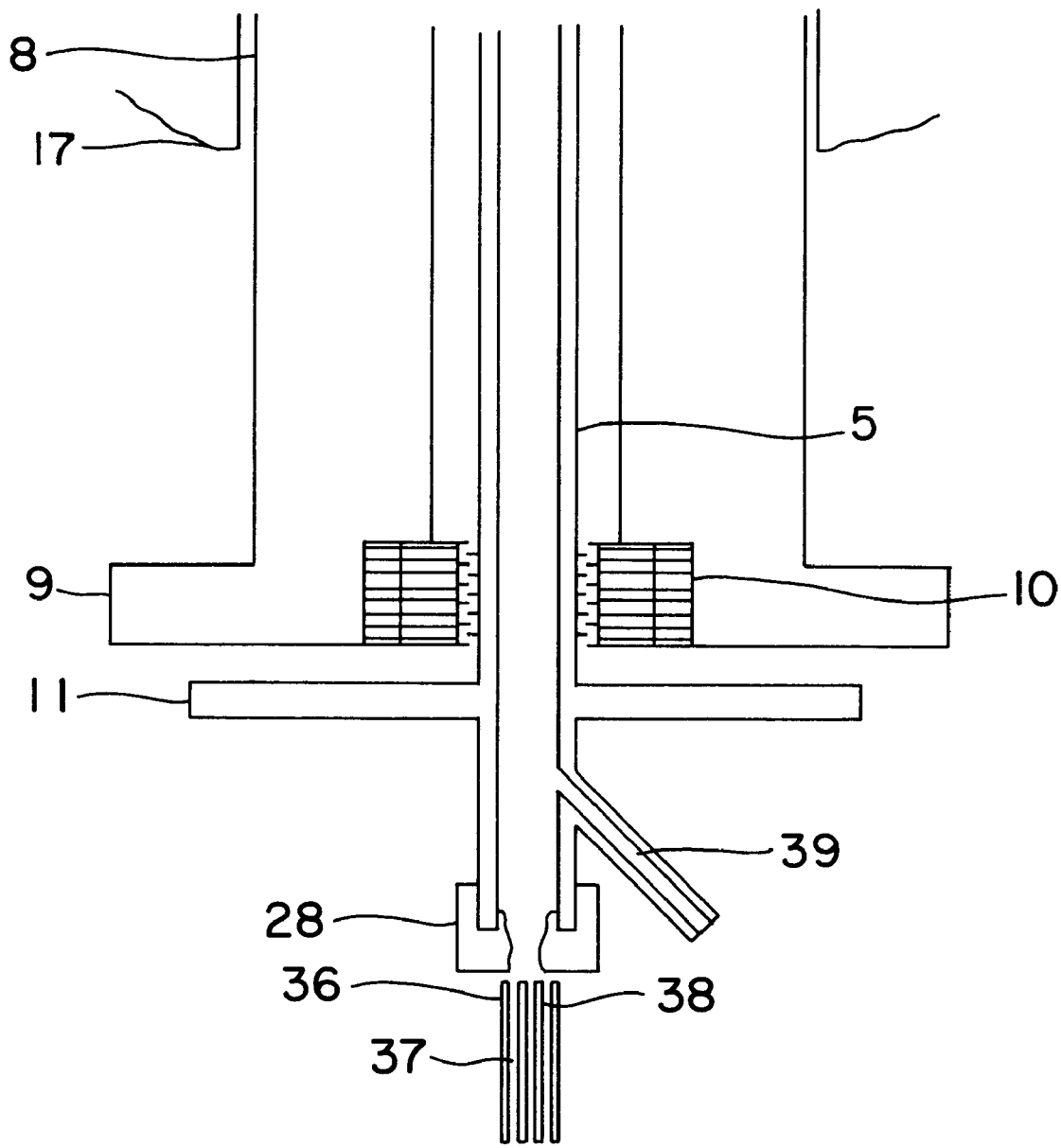

FIG. 9 shows the lower region of the transport catheter 8 with a guide 5, which is set up for the insertion of a probe 36 with flexible optics and a rinsing conduit. The probe 36 has the flexible optics 37 and a rinsing fluid supply 38. The rinsing fluid discharge 39 is disposed on the guide shaft 5. A sealing fitting 28 is provided for the probe 36. An apparatus of this kind is advised for probing and precise positioning when there are difficult pathological conditions or when optics are required for the recognition of suspected constrictions, tumors, and the like inside the urethra, and when a rinsing should be required.

Figure 10:
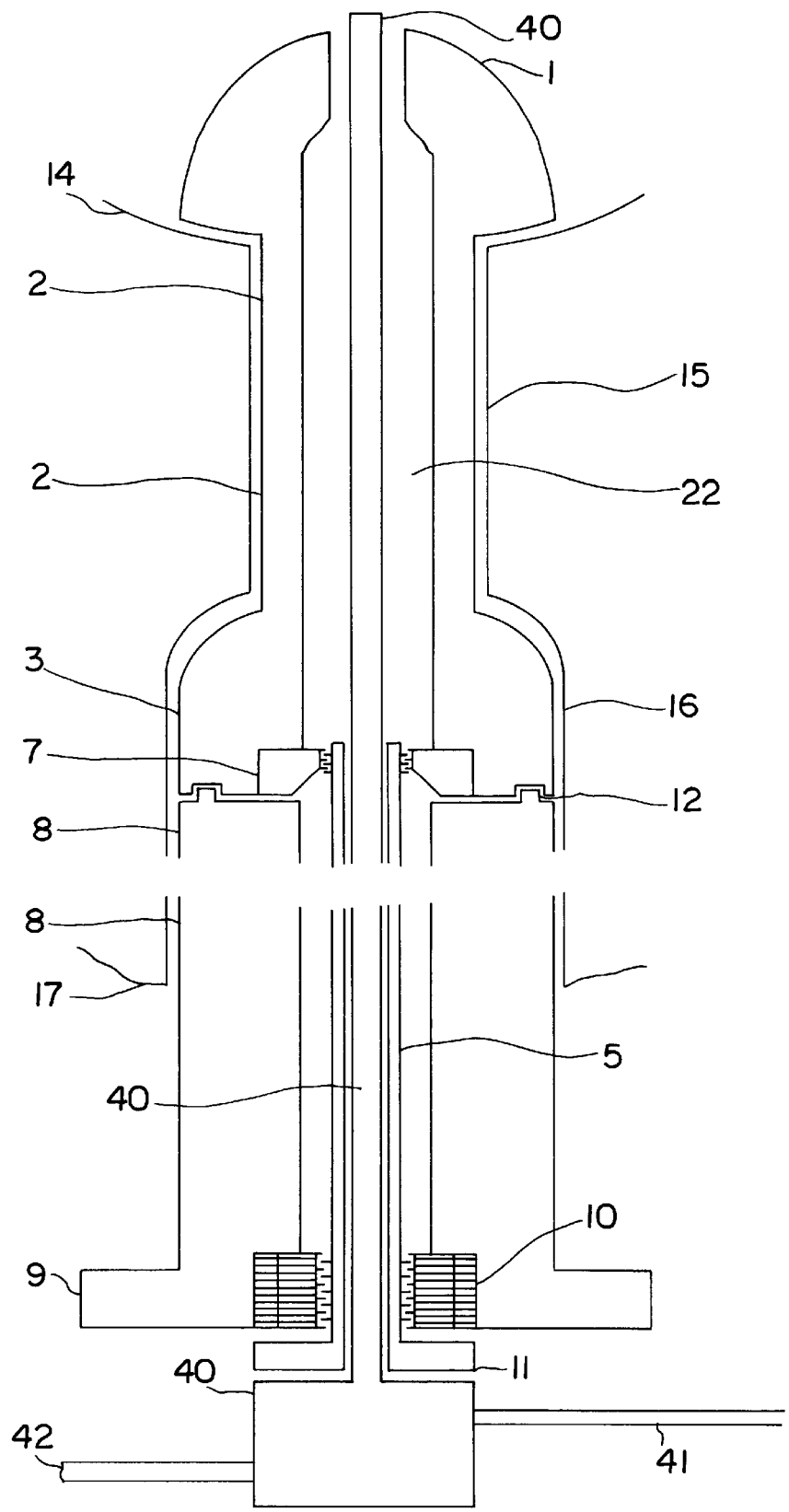

FIG. 10 essentially contains the combination of embodiments according to FIGS. 3 and 9; a probe 40 with optics and a rinsing conduit outside the urethra is connected with a connecting cable 41 to a monitor not shown and further connected to a rinsing fluid supply line 42. The probe 40 is passed to the outside in an upward direction by means of the IUC 1–3 and consequently ends in the bladder interior. This can bring about the correct placement of the IUC using visual assistance.

When introducing administered radiographic contrast medium solutions, the entire procedure can be made essentially easier by making the urethral and bladder conditions visible as well as by means of the lubrication function that a radiographic contrast medium of this kind has.

As long as a guide is provided, it can be elongated to the point that it reaches into the IUC and stiffens it.

The IUC can also be embodied as a tube with ribs running longitudinally to produce corresponding through flow openings. It is generally true that the invention can be employed with IUCs of any form, that is it can be used along with IUCs of this kind.

All features shown and described as well as their combination with one another, are essential to the invention. Also, features shown in one of the exemplary embodiments can analogously be used in one of the other exemplary embodiments and vice versa.

What is claimed is:

1. An apparatus for maintaining the patency of urine flow through a human urethra and urethral orifice, having:
   (a) an intra-urethral catheter (IUC), which has a potential through flow for the urine that extends over its length, whose length is adapted to be shorter than the average length of an adult male urethra, and which does not protrude from the urethral orifice when in position in the urethra, said IUC having a proximal end (3) positionable toward a doctor when the IUC is in position in the urethra; and
   (b) a transport means for the insertion of the IUC into the urethra, said transport means having a distal end positionable toward a patient when the IUC is in position in the urethra;
   (c) an actuator for producing and detaching a connection between the proximal end of the IUC and the distal end of the transport means.

2. The apparatus of claim 1, wherein the length of the IUC is matched to the length of a constriction that exists in the urethra or is matched to the length of a particular section of the urethra and the outer diameter of the IUC approximately corresponds to the inner diameter of a healthy urethra that is not narrowed.

3. The apparatus of claim 2, wherein the length of the IUC is matched to the length of a prostate gland with affiliated inner and outer sphincters.

4. The apparatus according to claim 2, wherein the length of the IUC is matched to the length of the prostate gland including the inner sphincter.

5. The apparatus as defined in claim 4, characterized in that the IUC in the form of the IUCI or IUCP is thickened on both ends and that the length of the narrowed section disposed between them is the same as the effective length of the relevant IUC, wherein in use the end of the IUC oriented toward the patient is lengthened beyond the region of the outer sphincter.

6. The apparatus according to claim 5, characterized in that the thickened ends (1, 3) of the IUC are embodied as sturdy and comprise one piece of plastic with the narrowed section (2).

7. The apparatus according to claim 6, characterized in that the thickened ends (3) of the IUC comprise a different plastic from its narrowed section, wherein the elasticity of the plastic of the thickened ends is greater than the elasticity of the narrowed section.

8. The apparatus according to claim 5 characterized in that the potential through flow is a central opening which passes through the IUC from both face ends of the thickened, sturdy ends (1, 3).

9. The apparatus according to one of claims 1 characterized in that the narrowed section (2) of the IUC comprises metal, to which are affixed thickened ends (1, 3) made of an elastic plastic.

10. The apparatus according to claim 9 characterized in that a retractor sleeve (21) and a retractor part (20), which is supported so that it can move longitudinally in this sleeve, are disposed in the continuously hollow inner chamber of the transport catheter (8) as a detachable connection between IUC and transport catheter, and that means are provided for pulling the retractor wedge downward into the retractor sleeve in order to spread this out against a stop of the IUC or its inner wall and to thus clamp it.

11. The apparatus according to claim 1, characterized in that an IUC, which is called an "IUCU" and can be positioned in the frontal urethra, is provided in the form of a tube (30, 31) whose elastic walls are preformed so that they curve outward and hence give the IUCU a more or less oval cross sectional shape when it is relaxed and that the length of this tube (30, 31) can be changed by stretching, whereupon its outer and inner diameter correspondingly change along with it.

12. The apparatus according to claim 11, characterized in that on its outer surface, the tube (30, 31) is provided with projections, knobs, or the like for contacting the dilated region of the urethra wall.

13. The apparatus according to claim 11, characterized in that a plunger (47) is provided for changing the length of the tube (30, 31), which plunger engages the end of the tube (30) oriented toward the patient, while the end of the tube (30) oriented toward the doctor is detachably connected to the transport means.

14. The apparatus according to claim 12 characterized in that the detachable connection of the IUC to the transport catheter is carried out by means of a balloon catheter which is disposed in a recess of the urethral stent and that a supply line comprising a hollow chamber in the balloon catheter shaft is provided for the supply of gaseous or liquid medium into the balloon or for the drainage of the medium from this balloon.

15. The apparatus according to claim 1 characterized in that a transport catheter (8) is provided as transport means, which has or carries detachable connecting means on the end oriented toward the patient, which together with mating connection means fitted to it on the end of the IUC oriented toward the doctor, constitute a detachable connection, wherein a device, which is made to fit the connecting means of the transport catheter and is to be actuated from the outside, is provided for producing and detaching this connection and is moved and carried along by the transport catheter.

16. The apparatus according to claim 15 characterized by means of a detachable screw connection between the IUC (1–3; 30, 30') and the transport catheter (8) or the connecting means carried by it.

17. The apparatus according to claim 16, characterized by means of a screw thread (26) in a stop, e.g. a metal ring, or by means of a thread made of the material of the relevant IUC and an opposite screw thread part (44) on the transport catheter or on a guide (5) carried by it.

18. The apparatus as defined in claim 15, characterized in that on the end oriented toward the doctor, the guide protrudes from the body and further comprises a handle for rotation of the guide; said guide being detachably screwed to the transport catheter and supported so that it can move in the lumen of the transport catheter, said guide defining a hollow portion in which a fitting is provided for the introduction of a radiographic contrast medium or a lubricant and a directional probe is supported so that it moves longitudinally in the lumen of this guide.

19. The apparatus according to claim 18, characterized in that on the end oriented toward the doctor, the detachable screw connection (10) between guide (5) and transport catheter (8) has the same thread turn direction and thread pitch as the threaded connection (26/44) between the IUC and the end of the guide (5') oriented toward the patient.

20. The apparatus according to claim 1 characterized in that for the IUC in the form of an IUCU, a movable guide (5) is provided and embodied on the end of the IUCU oriented toward the patient as a sliding bolt (47) which can be moved by the guide and engages a stop of the IUCU for stretching the IUCU.

* * * * *